United States Patent
Ishikawa et al.

(10) Patent No.: US 10,458,947 B2
(45) Date of Patent: Oct. 29, 2019

(54) THINNING DETECTION SYSTEM AND THINNING DETECTION METHOD

(71) Applicant: Yokogawa Electric Corporation, Musashino-shi, Tokyo (JP)

(72) Inventors: Tetsuya Ishikawa, Musashino (JP); Shinya Mito, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 225 days.

(21) Appl. No.: 15/492,265

(22) Filed: Apr. 20, 2017

(65) Prior Publication Data

US 2017/0307566 A1  Oct. 26, 2017

(30) Foreign Application Priority Data

Apr. 22, 2016  (JP) ................................. 2016-085916

(51) Int. Cl.
*G01N 27/72* (2006.01)
*G01N 17/04* (2006.01)
(Continued)

(52) U.S. Cl.
CPC .............. *G01N 27/72* (2013.01); *G01N 17/00* (2013.01); *G01N 17/04* (2013.01); *G01N 27/82* (2013.01)

(58) Field of Classification Search
CPC ........ G01N 27/72; G01N 17/00; G01N 17/04; G01N 27/82
See application file for complete search history.

(56) References Cited

U.S. PATENT DOCUMENTS

| 6,501,266 B1* | 12/2002 | Krivoi | G01N 27/83 |
| | | | 324/229 |
| 2013/0124109 A1* | 5/2013 | Denenberg | G01N 17/04 |
| | | | 702/35 |
| 2017/0012793 A1 | 1/2017 | Morita et al. | |

FOREIGN PATENT DOCUMENTS

| JP | 64-481 A | 1/1989 |
| JP | 2007-327924 A | 12/2007 |

(Continued)

OTHER PUBLICATIONS

Communication dated Jul. 31, 2017 issued by the European Patent Office in counterpart European Patent Application No. 17167224.9.
(Continued)

*Primary Examiner* — Patrick Assouad
*Assistant Examiner* — Feba Pothen
(74) *Attorney, Agent, or Firm* — Sughrue Mion, PLLC

(57) ABSTRACT

A thinning detection system includes a current applying apparatus configured to apply an AC current to electrodes installed on metal equipment which is a monitoring object, a magnetic-field measuring apparatus including an array of magnetic sensors configured to measure a magnetic field distribution of a surface side of the metal equipment; and a measurement managing apparatus configured to estimate a thinning distribution of the metal equipment based on a magnetic field distribution difference which is a difference between a reference magnetic-field distribution which is obtained in a case where thinning has not occurred in the metal equipment and a measurement magnetic-field distribution which is an actual measurement result. The measurement managing apparatus calculates a virtual current distribution of the metal equipment from the magnetic field distribution difference, and estimates the thinning distribu- (Continued)

tion of the metal equipment on the basis of a virtual eddy current represented by the virtual current distribution.

8 Claims, 18 Drawing Sheets

(51) Int. Cl.
  *G01N 27/82* (2006.01)
  *G01N 17/00* (2006.01)

(56) References Cited

FOREIGN PATENT DOCUMENTS

| JP | 2013-224864 A | 10/2013 |
| JP | 2015-137930 A | 7/2015 |
| WO | 2015/111588 A1 | 7/2015 |
| WO | 2015111558 A1 | 7/2015 |
| WO | 2016199872 A1 | 12/2016 |

OTHER PUBLICATIONS

R. Amineh, et al; "A Space Mapping Methodology for Defect Characterization From Magnetic Flux Leakage Measurements"; IEEE Transactions on Magnetics; vol. 44; No. 8; Aug. 2008; pp. 2058-2065; 8 pgs. total.

A. Khodayari-Rostamabad, et al; "Machine Learning Techniques for the Analysis of Magnetic Flux Leakage Images in Pipeline Inspection"; IEEE Transactions on Magnetics; vol. 45; No. 8; Aug. 2009; pp. 3073-3084; 12 pgs. total.

Sekihara, K., "Imaging of source of magnetic field by living body magnetic field measurement", Nov. 1991, Optics, vol. 20, Issue No. 1, 17 pages total.

Communication dated Dec. 6, 2018, issued by the European Patent Office in counterpart European Application No. 17167224.9.

* cited by examiner

THINNING DETECTION SYSTEM AND THINNING DETECTION METHOD

CROSS-REFERENCE TO RELATED APPLICATION

The present application claims priority from Japanese Patent Application No. 2016-085916 filed on Apr. 22, 2016, the entire content of which is incorporated herein by reference.

BACKGROUND

Technical Field

The present invention related to a system and a method for detecting thinning of metal equipment attributable to corrosion or the like.

Related Art

In plants such as petroleum plants and petrochemical plants, if corrosion, particularly, local corrosion occurs at equipments such as metal pipelines, reaction apparatuses, and distillation columns, the corrosion may cause thinning of the equipments, resulting in leakage and a decrease in production efficiency. For this reason, in a case where local corrosion or the like occurs at equipments such as metal pipelines and huge reaction apparatuses extending throughout plants, resulting in thinning, it is required to early detect the thinning.

However, in a case where thinning occurs at the inside of a pipeline, the rear surface of a metal plate, or the like, it is difficult to visually find the thinning. For this reason, technologies for detecting occurrence of thinning at parts which are not directly observable have been developed.

For example, Japanese Patent Application Laid-Open No. 2015-137930 discloses a technology for performing thinning inspection by applying a reference current to an inspection object metal and detecting the density of magnetic flux caused by the reference current by a magnetic sensor. This technology is based on that, at a part where thinning has occurred, since the electric resistance increases, the current density distribution changes, and thus the magnetic field distribution (the magnetic flux density distribution) which is detected by the magnetic sensor also changes.

Change in the magnetic field distribution can be obtained on the basis of the difference between a magnetic field distribution detected during an inspection and a reference magnetic-field distribution obtained by applying the reference current to an unthinned metal.

Since the magnetic sensor can measure magnetic flux densities without contact with inspection object metals, according to the above-described technology, it is possible to prevent inspection object metals from being adversely affected by contact with a different metal. Also, even in a case where an inspection object metal is covered with a protecting material such as a lagging material or a coating, it is possible to perform thinning inspection without removing the protecting material.

[Patent Document 1] Japanese Patent Application Laid-Open No. 2015-137930

According to the technology for detecting thinning on the basis of change in magnetic field distribution, for example, at a part, if the magnetic field distribution has changed, it possible to estimate that thinning has occurred. However, it is impossible to immediately obtain the shape and depth of the thinning from the change in the magnetic field distribution.

In order to obtain the shape and depth of thinning from change in magnetic field distribution, for example, it can be considered to use a pattern matching technology. Since it has been found out by simulations that even though parts are the same in thinning depth, if they are different in thinning shape, they are significantly different in change in magnetic field distribution, in a case of performing a pattern matching scheme, with respect to each of a plurality of thinning patterns having different shapes, in advance, changes in magnetic field distribution are calculated at different depths by experiments, simulations, or the like. Thereafter, if change in magnetic field distribution is measured, the shape and depth of thinning are estimated by searching for a thinning pattern associated with a change in magnetic field distribution most similar to the measured change.

The pattern matching scheme has a feature in which, with respect to thinning which matches any one of prepared thinning patterns, it is possible to expect high estimation accuracy; whereas with respect to thinning which does not match any one of prepared thinning patterns, estimation accuracy markedly decreases.

The shape of thinning which actually occurs in metal equipment is of great variety, and thus it is not realistic to prepare a change in magnetic field distribution with respect to every thinning pattern. For this reason, it has been desired to develop a thinning estimation technology coping with various thinning shapes.

SUMMARY

Exemplary embodiments of the invention provide a thinning detection system and method for performing thinning estimation coping with various thinning shapes.

A thinning detection system according to an exemplary embodiment, comprises:

a current applying apparatus configured to apply an AC current to electrodes installed on metal equipment which is a monitoring object;

a magnetic-field measuring apparatus including an array of magnetic sensors configured to measure a magnetic field distribution of a surface side of the metal equipment; and a measurement managing apparatus configured to estimate a thinning distribution of the metal equipment on the basis of a magnetic field distribution difference which is a difference between a reference magnetic-field distribution which is obtained in a case where thinning has not occurred in the metal equipment and a measurement magnetic-field distribution which is an actual measurement result, wherein the measurement managing apparatus calculates a virtual current distribution of the metal equipment from the magnetic field distribution difference, and estimates the thinning distribution of the metal equipment on the basis of a virtual eddy current represented by the virtual current distribution.

The measurement managing apparatus may be configured to:

estimate a thinning shape on the basis of a spiral shape of the virtual eddy current; and estimate a thinning depth on the basis of a density of the virtual eddy current.

The measurement managing apparatus may be configured to:

approximate a current path of the metal equipment by an oriented square lattice; and calculate the virtual current distribution by solving a quadratic programming problem for minimizing a distance between the magnetic field distribution difference and a magnetic flux density distribution on each magnetic sensor caused by the virtual current distribution under a constraint condition which is a current conservation law for each node of the oriented square lattice.

The measurement managing apparatus may be configured to correct the measurement magnetic-field distribution on the basis of positions of the magnetic sensors and the metal equipment.

With respect to a certain magnetic sensor, on the basis of magnetic flux densities obtained by AC currents with different frequencies applied to the metal equipment, the measurement managing apparatus may be configured to calculate the positions of the corresponding magnetic sensor and the metal equipment.

The measurement managing apparatus may be configured to calculate the positions of a certain magnetic sensor and the metal equipment on the basis of a magnetic flux density measured by the corresponding magnetic sensor, and a magnetic flux density measured by an auxiliary magnetic sensor disposed on the extension of the corresponding magnetic sensor from the metal equipment.

A thinning detection method according to an exemplary embodiment, comprises:

applying an AC current to electrodes installed on metal equipment which is a monitoring object;

measuring a magnetic field distribution of a surface side of the metal equipment by an array of magnetic sensors; and estimating a thinning distribution of the metal equipment on the basis of a magnetic field distribution difference which is a difference between a reference magnetic-field distribution which is obtained in a case where thinning has not occurred in the metal equipment and a measurement magnetic-field distribution which is an actual measurement result, wherein the thinning estimation calculates a virtual current distribution of the metal equipment from the magnetic field distribution difference, and estimates the thinning distribution of the metal equipment on the basis of a virtual eddy current represented by the virtual current distribution.

According to the present invention, it is possible to provide a thinning detection system and method for performing thinning estimation coping with various thinning shapes.

DETAILED DESCRIPTION

Figure 1:
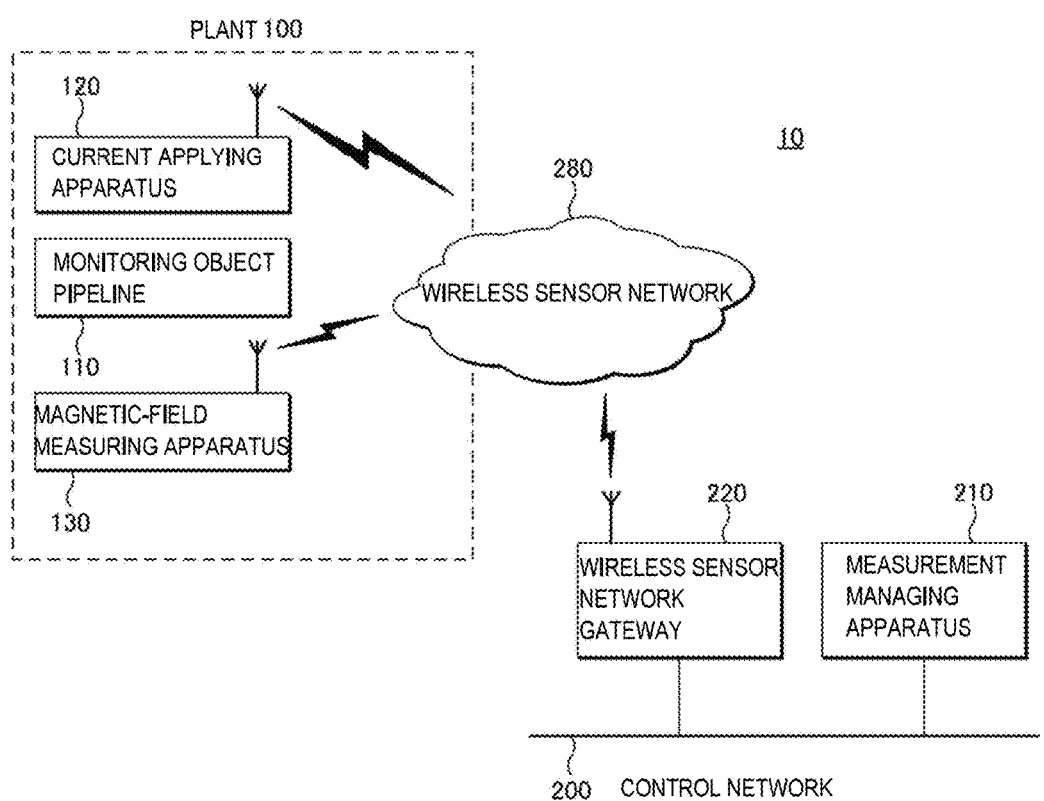
FIG. 1 is a block diagram illustrating the configuration of a thinning detection system according to an embodiment.

An embodiment of the present invention will be described with reference to the accompanying drawings. FIG. 1 is a block diagram illustrating the configuration of a thinning detection system 10 according to the present embodiment. The thinning detection system 10 is a system for performing thinning detection on a metal pipeline (referred to as the monitoring object pipeline 110) laid in a plant 100. In the present embodiment, the metal pipeline will be described as an example of a thinning detection object; however, the thinning detection system 10 is not limited to the metal pipeline, and can perform thinning detection on metal equipment such as a distillation column or a reaction apparatus.

As shown in FIG. 1, the thinning detection system 10 includes a current applying apparatus 120 and a magnetic-field measuring apparatus 130 which are disposed in the vicinity of the monitoring object pipeline 110 of the plant 100, and a measurement managing apparatus 210 connected to a control network 200.

The current applying apparatus 120 and the magnetic-field measuring apparatus 130 have a wireless communication function. Also, the measurement managing apparatus 210 is connected to a wireless sensor network gateway 220 by the control network 200. In this way, the measurement managing apparatus 210, the current applying apparatus 120, and the magnetic-field measuring apparatus 130 are configured to perform wireless communication with one another by a wireless sensor network 280. However, these apparatuses may perform wire communication with one another.

The wireless sensor network 280 can use an industrial wireless sensor network such as ISA100.11a or WirelessHART, or a general-purpose wireless network such as IEEE 802.11 or IEEE 802.15.4.

Figure 2:
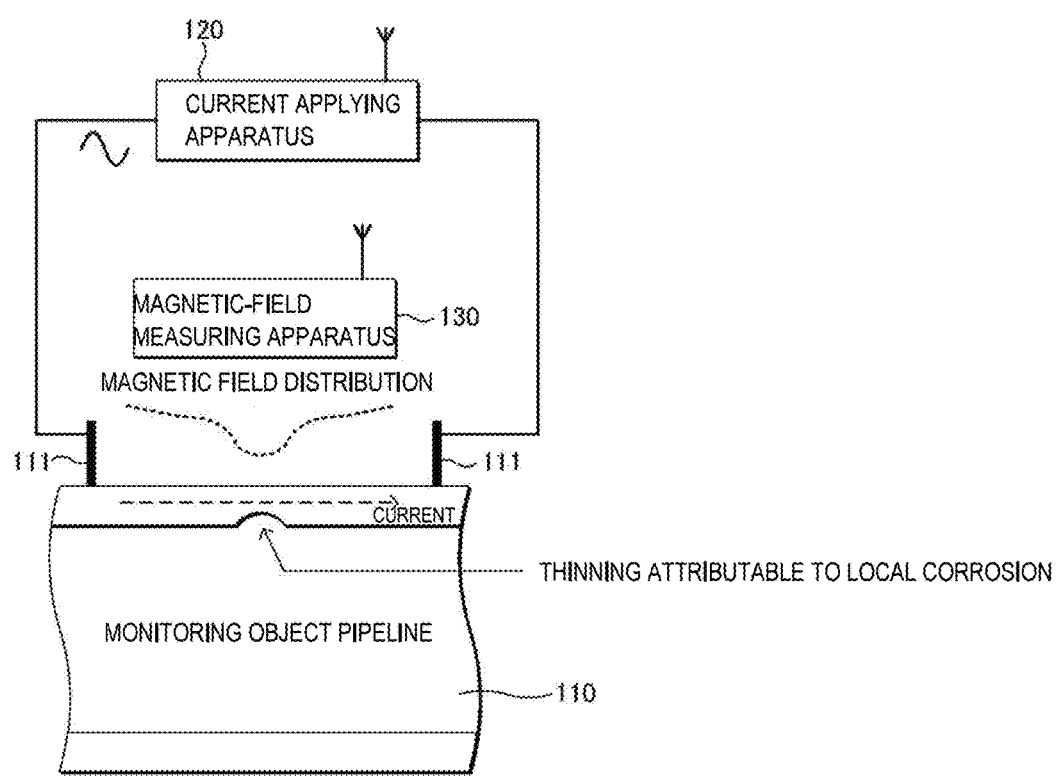
FIG. 2 is a view for explaining functions of a current applying apparatus and a magnetic-field measuring apparatus on a monitoring object pipeline.

As shown in FIG. 2, in the thinning detection system 10 of the present embodiment, the current applying apparatus 120 applies an AC current to the metal surface of the monitoring object pipeline 110 through a pair of electrodes 111 provided on the metal surface of the monitoring object pipeline 110. The magnetic-field measuring apparatus 130 is disposed in the vicinity of the monitoring object pipeline 110, and measures a magnetic field distribution.

The current applied to the monitoring object pipeline 110 flows at a current density according to the resistance distribution of the metal surface, thereby producing a magnetic field. At this time, if a part of the monitoring object pipeline 110 has been thinned by corrosion or the like, since the resistance of the corresponding part changes, the current density distribution changes, and the magnetic field distribution also changes. A method of estimating a thinning distribution, that is, the position, shape, and depth of thinning from a change in the magnetic field distribution will be described below.

Figure 3:
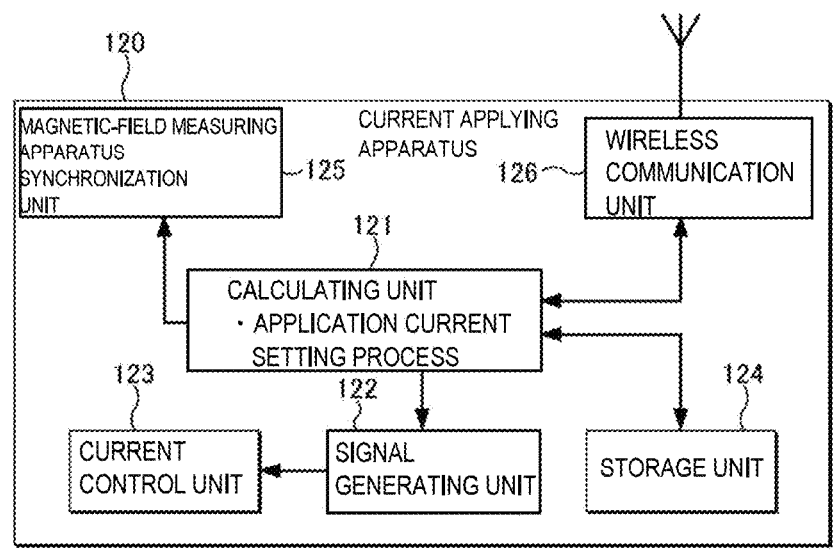
FIG. 3 is a block diagram illustrating a configuration example of the current applying apparatus.

FIG. 3 is a block diagram illustrating a configuration example of the current applying apparatus 120. As shown in FIG. 2, the current applying apparatus 120 includes a calculating unit 121, a signal generating unit 122, a current control unit 123, a storage unit 124, a magnetic-field measuring apparatus synchronization unit 125, and a wireless communication unit 126.

The calculating unit 121 performs various processes such as a process of setting the current value, frequency, and the like of a current to be applied, on the basis of setting information transmitted from the measurement managing apparatus 210. The signal generating unit 122 generates a current waveform to be applied, on the basis of the setting of the calculating unit 121. The current control unit 123 controls the application current on the basis of the current waveform generated by the signal generating unit 122. The setting information such as the set current value is stored in the storage unit 124. The magnetic-field measuring apparatus synchronization unit 125 performs a process of performing synchronization with the magnetic-field measuring apparatus 130. The wireless communication unit 126 performs a process of establishing a connection with the wireless sensor network 280.

In general, magnetic field measurement is affected by environmental magnetic fields such as the earth's magnetism. For this reason, it is preferable that a current which the current applying apparatus 120 applies have, for example, a frequency other than the integral multiples of a commercial frequency such as 50 Hz or 60 Hz, or a frequency at which signal selectivity is good, such as a prime number frequency.

Figure 4:
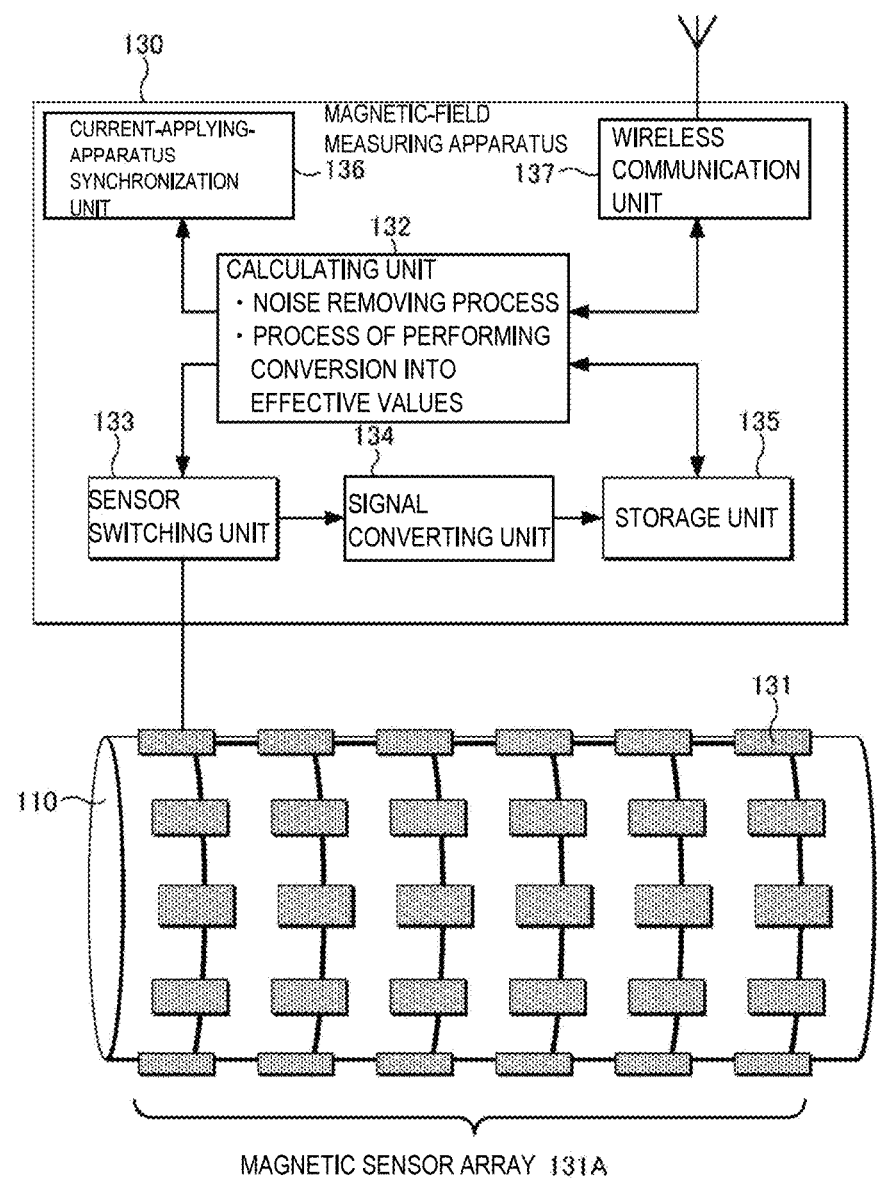
FIG. 4 is a block diagram illustrating a configuration example of the magnetic-field measuring apparatus.

FIG. 4 is a block diagram illustrating a configuration example of the magnetic-field measuring apparatus 130. As shown in FIG. 4, the magnetic-field measuring apparatus 130 includes a magnetic sensor array 131A, a calculating unit 132, a sensor switching unit 133, a signal converting unit 134, a storage unit 135, a current-applying-apparatus synchronization unit 136, and a wireless communication unit 137.

The magnetic sensor array 131A is an array of magnetic sensors 131 for detecting a magnetic flux density, and is attached to the monitoring object pipeline 110 as shown in FIG. 4. By the magnetic sensor array, it is possible to obtain the magnetic field distribution (magnetic flux density distribution) of the surface of the monitoring object pipeline 110. The magnetic sensors 131 are sensors having a small size and low power consumption, and thus can be densely mounted in a large area. Therefore, it is possible to measure a magnetic field distribution with a high surface resolution.

The magnetic sensor array 131A may be always attached to the monitoring object pipeline 110. In this case, it is possible to save the effort of attaching the magnetic sensors to the monitoring object pipeline 110 whenever measurement is performed, and it is possible to continuously perform measurement.

The sensor switching unit 133 performs switching to magnetic sensors 131 to be measurement value acquisition objects, with respect to the magnetic sensors 131 constituting the magnetic sensor array 131A. In other words, in the present embodiment, measurement values are sequentially acquired from the magnetic sensors. As measurement value acquiring methods, there are a method of sequentially acquiring measurement values from the magnetic sensors 131 as in the present embodiment, and a method of acquiring measurement values at the same time, and since change in thickness attributable to corrosion is generally slow, and it is possible to reduce the cost of circuit components, in the present embodiment, the method of sequentially acquiring measurement values is described. Needless to say, in order to reduce measurement time, it is possible to acquire measurement values from the magnetic sensors 131 at the same time.

The signal converting unit 134 converts measurement values into digital signals. The storage unit 135 is for storing measurement values converted into digital signals, setting information for measurement, and so on. The calculating unit 132 performs a process of removing noise from measurement values and converting the measurement values into effective values, processing on setting information, and so on. Specific methods of removing noise will be described below. The current-applying-apparatus synchronization unit 136 performs a process of performing synchronization with the current applying apparatus 120. The wireless communication unit 137 performs a process of establishing a connection with the wireless sensor network 280.

According to this configuration, if the current applying apparatus 120 applies an AC current, whereby an AC magnetic field is produced, the magnetic-field measuring apparatus 130 measures the AC magnetic field by the magnetic sensor array 131A. Thereafter, the magnetic-field measuring apparatus performs a noise removing process (to be described below) on the measurement results, and then performs a process of converting the measurement results into effective values. The magnetic-field measuring apparatus 130 transmits, for example, an array of the effective values corresponding to the magnetic sensors 131 of the array, as the measurement result to the measurement managing apparatus 210 through the wireless sensor network 280.

In the present embodiment, the current applying apparatus 120 and the magnetic-field measuring apparatus 130 are configured as separate and independent apparatuses. The first reason is that they are assured to be operated in an explosion-proof area of the petroleum industry, the petrochemical industry, or the like. The current applying apparatus 120 needs to handle a larger amount of electric power as compared to the magnetic-field measuring apparatus 130, and separation of these apparatuses makes it possible to simplify their circuit configurations and limit circuits which should be considered during a breakdown.

The second reason is that they are different in coverage. The current applying apparatus 120 can basically cover an area between the electrodes 111, and can easily cover a relatively large area.

Meanwhile, since the magnetic-field measuring apparatus 130 measures a magnetic field of a range which is covered by the array of the magnetic sensors 131, in order to expand its measurement area, it is required to increase the number of magnetic sensors of the magnetic sensor array 131A. Therefore, the area expansion is not easy.

For these reason, if one current applying apparatus 120 and a plurality of magnetic-field measuring apparatuses 130 are separately configured and operated, it is possible to easily expand the measurement area without scaling up the current applying apparatus 120. Needless to say, in order to save housing cost and space, the current applying apparatus 120 and the magnetic-field measuring apparatus 130 may be integrally configured.

In order to measure a magnetic field, the current applying apparatus 120 and the magnetic-field measuring apparatus 130 need to operate in sync with each other so as to apply a current at a magnetic-field measurement timing. Since their electronic circuits are separated, as the synchronization method, a method of applying a trigger by communication using light such as infrared light, or a synchronization method using the wireless sensor network 280 can be considered. In order to perform such a process, the magnetic-field measuring apparatus synchronization unit 125 is included in the current applying apparatus 120, and the current-applying-apparatus synchronization unit 136 is included in the magnetic-field measuring apparatus 130.

Specifically, a method of defining those apparatuses as a main apparatus and a sub apparatus, respectively, and setting a start timing and an operation time for the main apparatus (for example, the magnetic-field measuring apparatus 130), and performing synchronization with reference to the main apparatus can be considered. Also, after synchronization of the measurement managing apparatus 210 through the wireless sensor network 280 is performed, in order to more efficiently consume electric power, the current applying apparatus 120 and the magnetic-field measuring apparatus 130 may be locally synchronized through the synchronization units. In the present embodiment, the measurement managing apparatus 210 transmits the start timing and the operation time as setting information to both of the current applying apparatus 120 and the magnetic-field measuring apparatus 130. For this reason, the magnetic-field measuring apparatus synchronization unit 125 and the current-applying-apparatus synchronization unit 136 may be omitted.

Figure 5:
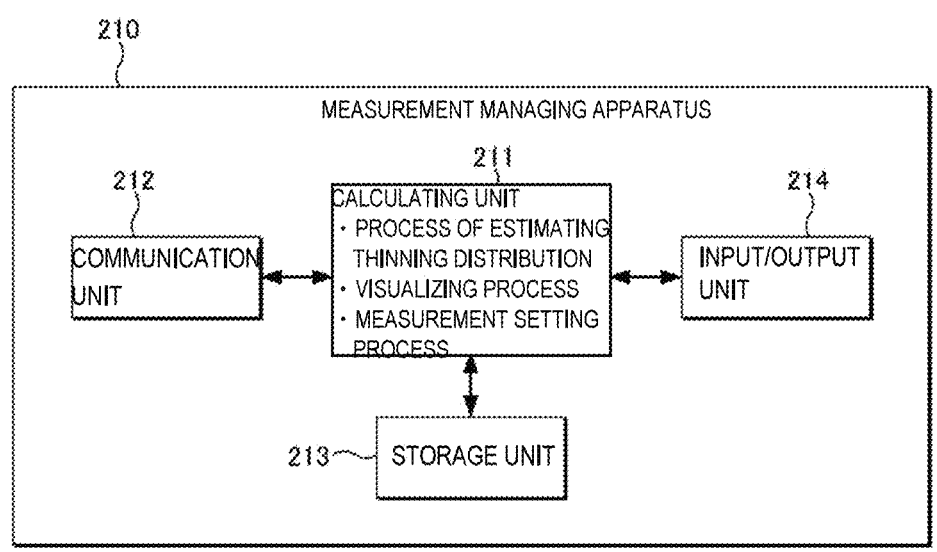
FIG. 5 is a block diagram illustrating a configuration example of a measurement managing apparatus.

FIG. 5 is a block diagram illustrating a configuration example of the measurement managing apparatus 210. As shown in FIG. 5, the measurement managing apparatus 210 includes a calculating unit 211, a communication unit 212, a storage unit 213, and an input/output unit 214.

The communication unit 21 performs a communication process through the control network 200. The storage unit 213 is for storing the relative positions of the magnetic-field measuring apparatus 130 and the monitoring object pipeline 110 installed in the plant 100, a variety of settings of the thinning detection system 10, an array of effective values received from the magnetic-field measuring apparatus 130 through the wireless sensor network, calculation results of the calculating unit 211, and so on.

The calculating unit 211 performs a process of estimating the distribution of thinning having occurred in the monitoring object pipeline 110, that is, the position, shape, and depth of the thinning, on the basis of the effective value array received from the magnetic-field measuring apparatus 130, a process of visualizing the thinning distribution, and a measurement setting process of setting the next measurement timing for the current applying apparatus 120 and the magnetic-field measuring apparatus 130, on the basis of the thinning state. The input/output unit 214 receives user's operations, and performs a process of outputting information obtained by visualizing the thinning distribution which is the process result of the calculating unit 211. The visualization of the thinning distribution can be performed by three-dimensional mapping, color mapping, or the like. Also, in the present embodiment, the measurement managing apparatus 210 and the input/output unit 214 for receiving user's operation are integrally configured; however, a separate input/output unit may be prepared and be connected to the measurement managing apparatus, for example, by the control network 200.

In a case of performing three-dimensional mapping as the visualization of the thinning distribution, for example, the shape and size of the thinning calculated are mapped with the shape of the monitoring object pipeline 110. In the measurement setting process, from the shape and size of the thinning, the depth in the thickness direction and a sectional loss rate are calculated. Also, these are compared with a thinning depth and a sectional loss rate calculated at the previous time, whereby change rates per unit time are calculated. Further, these are compared with a minimum allowable thickness and a maximum allowable shearing stress, whereby temporal margins are calculated, and on the basis of a smaller one of those margins, the next measurement timing is set for the current applying apparatus 120 and the magnetic-field measuring apparatus 130.

Now, a principle by which the thinning detection system 10 of the present embodiment estimates the thinning distribution, that is, the position, shape, and depth of the thinning on the basis of the change in the magnetic field distribution will be described. The thinning detection system 10 performs thinning distribution estimation using a virtual eddy current method newly developed in association with the present invention by the inventors of this application.

Here, the virtual eddy current is an eddy-like virtual current which corresponds to the position, shape, and depth of the thinning and is obtained by subtracting a current distribution obtained before the thinning occurred from a current distribution obtained when the thinning occurred. The present invention is based on that the virtual eddy current is highly correlated with the thickness.

Figure 6A:
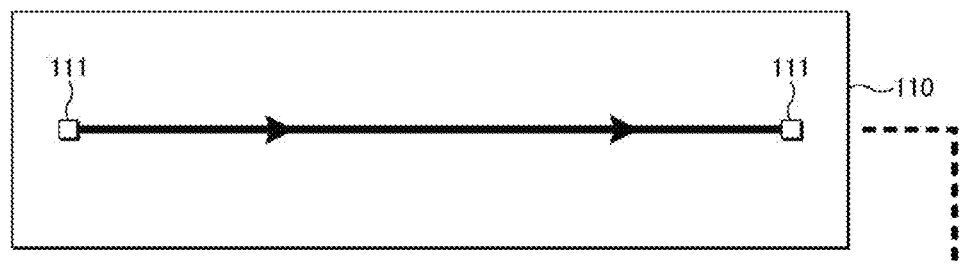
FIGS. 6A to 6C are views for explaining a virtual eddy current.
Figure 6B:
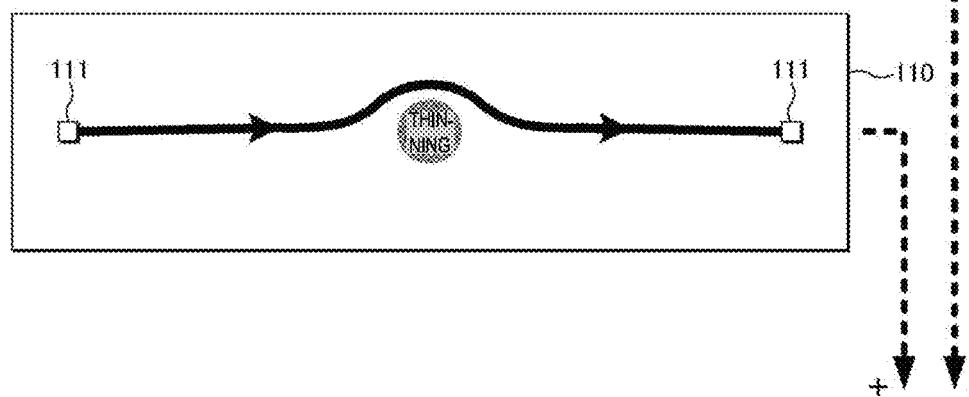
Figure 6C:
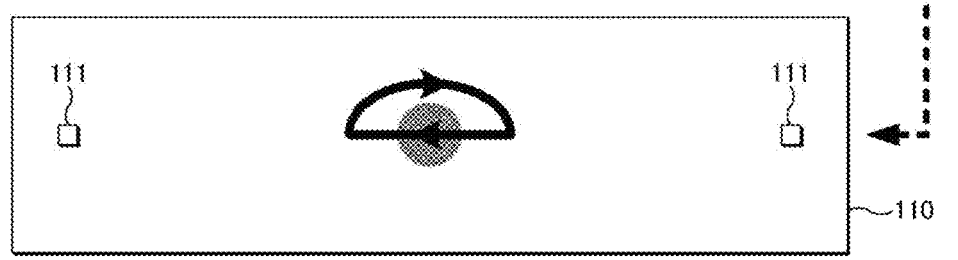

For example, in a case where a constant current flows between the electrodes 111 of the monitoring object pipeline 110, a difference between a current distribution of the monitoring object pipeline 110 obtained in a state where there is no thinning and shown in FIG. 6A and a current distribution of the monitoring object pipeline 110 obtained in a state where there is thinning and shown in FIG. 6B is considered. Since the amount of current which is applied from the electrodes 111 is constant, a virtual current which is obtained as the difference becomes an eddy-like current as shown in FIG. 6C without inflow and outflow through the electrodes 111. In the present invention, the virtual eddy-like current is referred to as the virtual eddy current.

From the results of numerical value simulations, it was found that such a virtual current is highly correlated with thinning. Specifically, it was found that the current density of a part of the virtual eddy current represents the amount of thinning of the corresponding part, and the spiral direction of the virtual eddy current represents the shape of the thinning. In other words, it is possible to estimate the position, shape, and depth of the thinning by obtaining the virtual eddy current.

Therefore, in the present embodiment, the magnetic field distribution of the monitoring object pipeline 110 in which thinning has not occurred is obtained in advance by a simulation or the like, and a difference between that magnetic field distribution and a magnetic field distribution obtained during an inspection is calculated. This magnetic field distribution difference can be regarded as a magnetic field distribution caused by the virtual eddy current. Therefore, the magnetic field distribution difference is converted into the virtual eddy current, and from the obtained virtual current, the thinning distribution is estimated.

Figure 7:
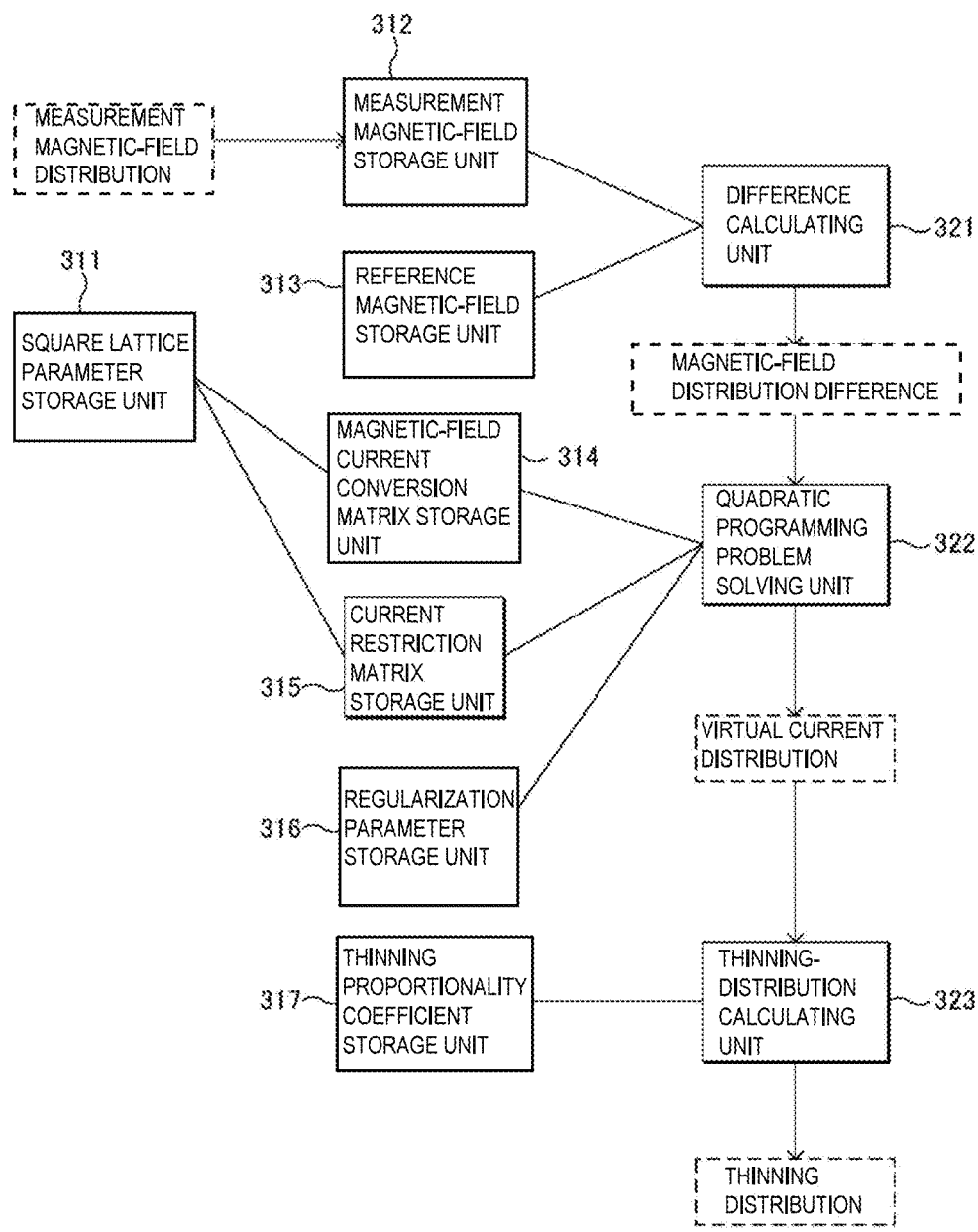
FIG. 7 is a view illustrating blocks for a thinning distribution estimating function which are formed in the measurement managing apparatus.

In order to perform these processes, in the calculating unit 211 and the storage unit 213 of the measurement managing apparatus 210, functional blocks as shown in FIG. 7 are formed. In other words, in the storage unit 213, a square lattice parameter storage unit 311, a measurement magnetic-field storage unit 312, a reference magnetic-field storage unit 313, a magnetic-field current conversion matrix storage unit 314, a current restriction matrix storage unit 315, a regularization parameter storage unit 316, and a thinning proportionality coefficient storage unit 317 are formed, and in the calculating unit 211, a difference calculating unit 321, a quadratic programming problem solving unit 322, and a thinning-distribution calculating unit 323 are formed.

The square lattice parameter storage unit 311 is for storing the size of an oriented square lattice which is used in the quadratic programming problem solving unit 322.

Figure 8:
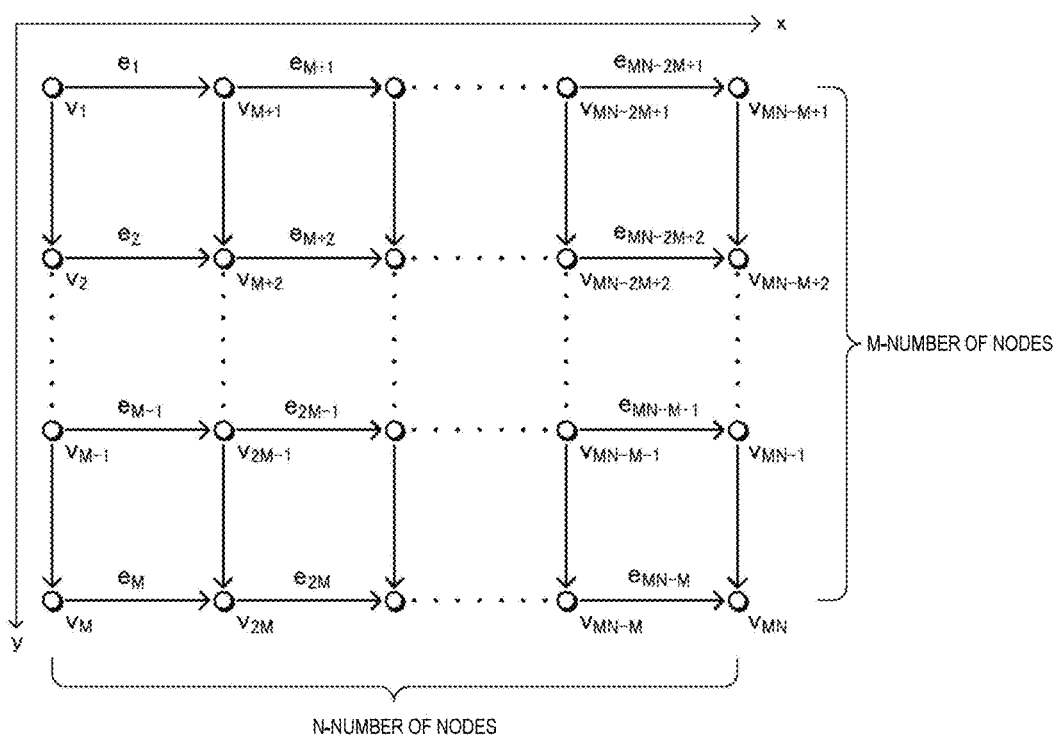
FIG. 8 is a view for explaining an oriented square lattice.

Now, the oriented square lattice will be described. The oriented square lattice is a graph which is used to model a current which virtually flows in the monitoring object pipeline 110 and is determined by (M×N)-number of nodes v and (2MN-M-N)-number of edges e as shown in FIG. 8. It is assumed that the current flows in the edges e provided as paths in a lattice shape and parallel to an x axis and a y axis. Also, in FIG. 8, in order to avoid complexity, edges e extending in the x axis direction are denoted by identifiers "$e_1$" to "$e_{MN-M}$", and edges e extending in the y axis direction are denoted by identifiers "$e_{MN-M+1}$" to "$e_{2MN-M-N}$". Also, the distance between neighboring nodes v in the x axis direction is represented by $w_x$, and the distance between neighboring nodes v in the y axis direction is represented by $w_y$.

As the number of nodes of the oriented square lattice, that is, (M×N) increases, current path resolution improves, and eddy current approximation accuracy improves; however, the amount of calculation increases in proportion to the increase in the number of nodes. Hereinafter, an oriented square lattice which is determined by a size stored in the square lattice parameter storage unit 311 will be referred to as a graph G (V, E). V is the whole set of the nodes v, and E is the whole set of the edges e.

Also, a current which flows in an edge $e_j$ will be referred to as $x_j$. Therefore, a virtual current distribution of the monitoring object pipeline 110 which is an object to be solved can be expressed by $x=(x_1, x_2, \ldots, x_{2MN-M-N})$.

The measurement magnetic-field storage unit 312 is for storing measurement magnetic-field distributions (arrays of effective value) measured by the magnetic-field measuring apparatus 130 during inspections. The reference magnetic-field storage unit 313 is for storing the magnetic field distribution (reference magnetic-field distribution) the monitoring object pipeline 110 in which thinning has not occurred. The magnetic field distribution in the state where thinning has not occurred can be obtained by actual measurement, a simulation, or the like.

The magnetic-field current conversion matrix storage unit 314 is for storing a magnetic-field current conversion matrix which is used to estimate a current distribution from the magnetic field distribution. Here, the magnetic field distribution is a magnetic field distribution which is measured by the magnetic-field measuring apparatus 130, and the current distribution is a virtual current distribution x of the monitoring object pipeline 110 to be solved.

The magnetic-field current conversion matrix is represented by $U(u_{ij})$. Here, $u_{ij}$ is the j-th column of the i-th row of the magnetic-field current conversion matrix U, and is a proportionality coefficient for associating a current flowing in an edge $e_j$ and the density of magnetic flux which is applied to the i-th magnetic sensor 131 by the corresponding current. In other words, the density of magnetic flux which is applied to a magnetic sensor i by a current $x_j$ flowing in the edge $e_j$ becomes $u_{ij} \times x_j$. The density of magnetic flux which is measured by the magnetic sensor i is the sum of the densities of magnetic fluxes which are applied by currents flowing in the individual edges. Therefore, the density of magnetic flux which is measured by the magnetic sensor i becomes $\Sigma(u_{ij} \times x_j)$.

Since $u_{ij}$ obeys Biot-Savart law representing magnitudes of magnetic fields which are produced by currents, $u_{ij}$ can be obtained on the basis of the coordinates of the magnetic sensors 131 of the magnetic sensor array 131A and the coordinates of the oriented square lattice of the monitoring object pipeline 110, by Expression 1.

$$u_{ij} = \frac{\mu_0}{4\pi((r_{ij}^y)^2 + (r_{ij}^z)^2)} \left[ \sqrt{\frac{(w_x - r_{ij}^x)^2}{(w_x - r_{ij}^x)^2 + (r_{ij}^y)^2 + (r_{ij}^z)^2}} + \sqrt{\frac{(r_{ij}^x)^2}{(r_{ij}^x)^2 + (r_{ij}^y)^2 + (r_{ij}^z)^2}} \right]$$ [Expression 1]

$r_{ij}^x$=(x coordinate of sensor i)–(x coordinate of start node of edge j)

$r_{ij}^y$=(y coordinate of sensor i)–(y coordinate of start node of edge j)

$r_{ij}^z$=(z coordinate of sensor i)–(z coordinate of start node of edge j)

$\mu_0$=magnetic permeability of vacuum

The current restriction matrix storage unit 315 is for storing a matrix which is an oriented-square-lattice connection matrix and represents currents flowing in the edges. Since currents flowing in the edges should satisfy Kirchhoff's laws, with respect to each node, it is required to express an inflow current and an outflow current. A current restriction matrix K ($=(k_{ij})$) can be expressed by Expression 2.

$$k_{ij} = \begin{cases} +1, & \text{current of edge } j \text{ flows into node } i, \\ -1, & \text{current of edge } j \text{ flows out of node } i, \\ 0, & \text{the others.} \end{cases}$$ [Expression 2]

The regularization parameter storage unit 316 is for storing a regularization parameter λ which is used by the quadratic programming problem solving unit 322. The regularization parameter λ will be described below. The thinning proportionality coefficient storage unit 317 is for storing a proportionality coefficient α which is used to calculate a thinning distribution from a calculated virtual eddy current. The proportionality coefficient α will be described below.

The difference calculating unit 321 calculates a magnetic-field distribution difference b which is a difference between the measurement magnetic-field distribution stored in the measurement magnetic-field storage unit 312 and the reference magnetic-field distribution stored in the reference magnetic-field storage unit 313.

The quadratic programming problem solving unit 322 calculates the virtual current distribution x from the magnetic-field distribution difference b calculated by the difference calculating unit 321, using the magnetic-field current conversion matrix U stored in the magnetic-field current conversion matrix storage unit 314, the current restriction matrix K stored in the current restriction matrix storage unit 315, and the regularization parameter λ stored in the regularization parameter storage unit 316.

The calculation of the virtual current distribution x from the magnetic field distribution difference is performed by solving a quadratic programming problem P shown by Expression 3.

$$P: \begin{cases} \min_{x} \ \|Ux - b\|^2 + \lambda \|x\|^2 \\ \text{s.t.} \quad Kx = 0, \end{cases} \quad \text{[Expression 3]}$$

Here, the constraint condition "Kx=0" is a condition for satisfying Kirchhoff's laws in which, with respect to each node, an inflow current and an outflow current are equal to each other.

The quadratic programming problem P is for obtaining such a virtual current distribution x at which a difference between a magnetic field distribution Ux which is caused by the virtual current distribution x and the magnetic-field distribution difference b is minimized, under the above-described constraint condition. However, in terms of mounting, the arrangement density of the magnetic sensors 131 is significantly lower than the density of the oriented square lattice. Therefore, it is impossible to determine only one optimal solution. For this reason, in order to select such a solution that the amount of eddy current which is generated is extremely small, a term using the regularization parameter λ is added as a regularization term to an evaluation expression.

The solution x of the quadratic programming problem P can be obtained by Expression 4. In Expression 4, S is a representation matrix of the kernel space of K. However, the solution x may be obtained by any other method. For example, many general quadratic programming problems can be solved by an infeasible primal-dual interior point method.

$$x = S(S^T U^T U S - \lambda S^T S)^{-1} S^T U^T b \quad \text{[Expression 4]}$$

The thinning-distribution calculating unit 323 calculates the thinning distribution from the virtual current distribution x representing the virtual eddy current. As described above, the current density of a part of the virtual eddy current represents the amount of thinning of the corresponding part, and the spiral direction of the virtual eddy current represents the shape of the thinning. Therefore, the thinning-distribution calculating unit 323 converts the virtual current distribution x into a matrix corresponding to the oriented square lattice, and multiplies the obtained matrix by the thinning proportionality coefficient α, thereby creating a thinning distribution matrix D, and converts the thinning distribution matrix into the position, shape, and depth of the thinning.

In advance, the thinning proportionality coefficient α is determined by performing a virtual eddy current method on a magnetic field acquired by a numerical value simulation such that the result of the virtual eddy current method coincides with the thinning distribution of the simulation, and is stored in the thinning proportionality coefficient storage unit 317.

The position, shape, and depth of the thinning represented by the thinning distribution matrix D can be visualized by displaying them by three-dimensional mapping, color mapping, or the like.

Since the thinning distribution estimation using the virtual eddy current as described above does not depend on specific thinning patterns, unlike a thinning detection method based on pattern matching, it is unnecessary to prepare specific thinning patterns in advance, and it is possible to perform thinning estimation coping with various thinning shapes.

Figure 9:
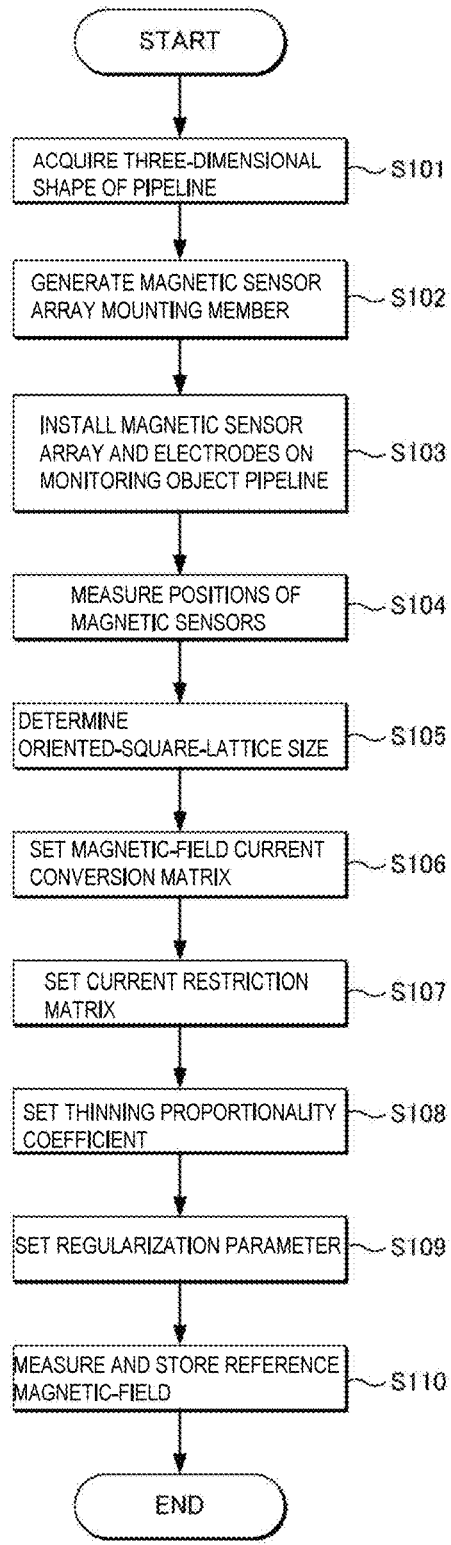
FIG. 9 is a flow chart for explaining a preparation phase before actual use of the thinning detection system.

Now, the operation of the thinning detection system 10 of the present embodiment will be described. First, a preparation phase before actual use will be described with reference to a flow chart of FIG. 9. In the preparation phase, the three-dimensional shape of the monitoring object pipeline 110 is acquired by measurement using a 3D scanner technology or on the basis of 3D CAD data used during manufacturing (STEP S101).

Subsequently, a member for mounting the magnetic sensor array 131A corresponding to the shape of the monitoring object pipeline 110 is generated (STEP S102). In a case of measuring the shape with a 3D scanner, it is possible to generate a member which is for mounting the magnetic sensor array 131A and corresponds even to distortion and the like of the monitoring object pipeline 110.

Also, in order to prevent the monitoring object pipeline 110 from being influenced by contact with a different metal, it is preferable that the mounting member have such a form that it is mounted in a point contact manner using legs, and as the mounting member, a member having such toughness that the positional relation between the magnetic sensors 131 and the monitoring object pipeline 110 does not change for a long period is used.

The magnetic sensors 131 are installed around the monitoring object pipeline 110, using the generated mounting member, and are connected to the magnetic-field measuring apparatus 130, and the electrodes 111 are attached to the surface, and are connected to the current applying apparatus 120 (STEP S103).

Subsequently, the relative position relation between each magnetic sensor 131 of the installed magnetic sensor array 131A and the monitoring object pipeline 110 is measured, and is recorded in the storage unit 213 (STEP S104). In a case where the positional relation between the monitoring object pipeline 110 and the magnetic sensors 131 is not preferable, correction, mounting adjustment, and the like on the mounting member are performed.

If the magnetic sensor array 131A is mounted on the monitoring object pipeline 110, an oriented-square-lattice size is determined, and is stored in the square lattice parameter storage unit 311 (STEP S105). It is assumed that the oriented-square-lattice size includes the number of nodes represented by MN, and the inter-node distances $w_x$ and $w_y$. As described above, the number of nodes represented by MN is determined in view of estimation accuracy and calculation time.

Subsequently, on the basis of the oriented-square-lattice size and the positions of the magnetic sensors 131, the magnetic-field current conversion matrix U is calculated, and is stored in the magnetic-field current conversion matrix storage unit 314 (STEP S106).

Also, on the basis of the oriented-square-lattice size, the current restriction matrix K is generated, and is stored in the current restriction matrix storage unit 315 (STEP S107).

Also, the thinning proportionality coefficient α is calculated by a magnetic field simulation, and is stored in the thinning proportionality coefficient storage unit 317 (STEP S108). As described above, the thinning proportionality coefficient α is determined by performing a virtual eddy current method on a magnetic field acquired by a numerical value simulation such that the result of the virtual eddy current method coincides with the thinning distribution of the simulation.

Also, the regularization parameter λ of the quadratic programming problem P is determined, and is stored in the square lattice parameter storage unit 311 (STEP S109).

Also, a constant current for measurement is applied to the monitoring object pipeline 110 in which thinning has not occurred, and a reference magnetic-field is measured, and is stored in the reference magnetic-field storage unit 313 (STEP S110). As the reference magnetic-field, a magnetic field distribution obtained by a simulation may be used. Also, with respect to the processes of STEPS S106 to S110, the order of the processes does not matter.

Figure 10:
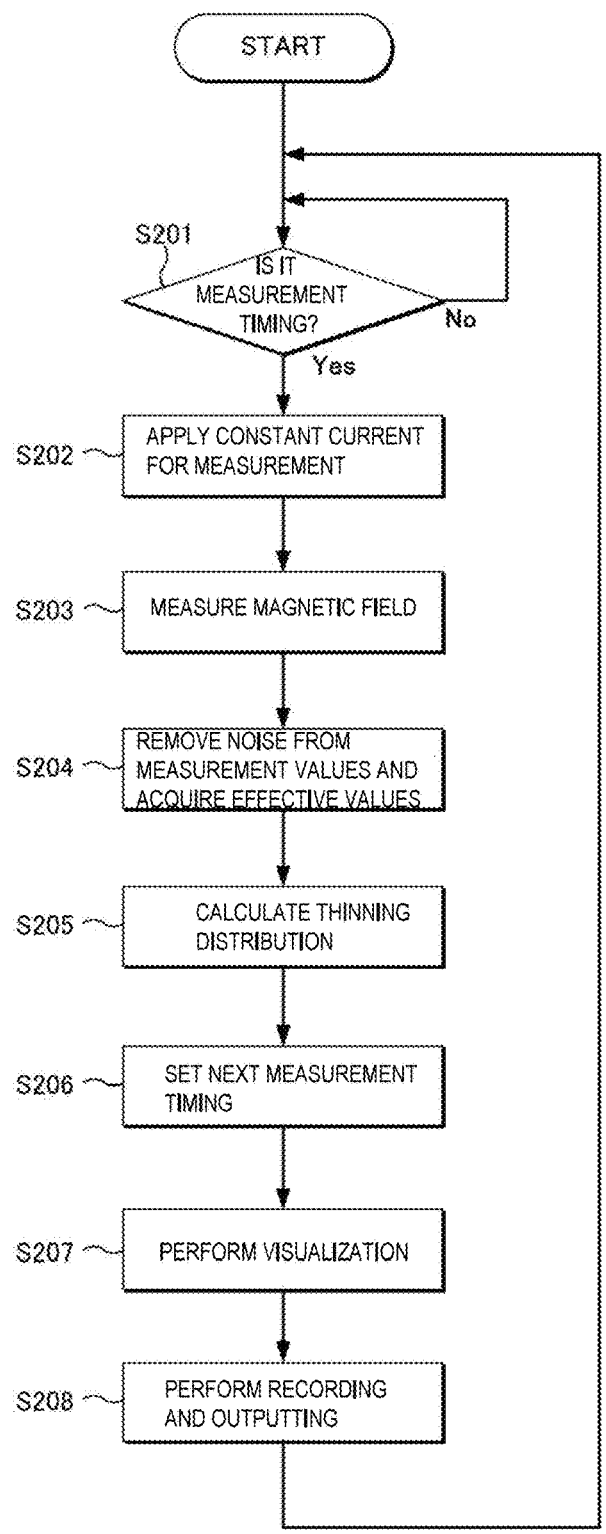
FIG. 10 is a flow chart for explaining the outline of an operation of the thinning detection system when the thinning detection system is used.

Now, the outline of the operation of the thinning detection system 10 during use will be described with reference to a flow chart of FIG. 10. If a predetermined measurement timing comes ("Yes" in STEP S201), the current applying apparatus 120 applies a predetermined current for measurement (STEP S202), and the magnetic-field measuring apparatus 130 measures a magnetic field distribution (STEP S203).

The calculating unit 132 of the magnetic-field measuring apparatus 130 removes noise from measurement values, thereby acquiring effective values (STEP S204). The effective values can be expressed in an array corresponding to the magnetic sensor array 131A, whereby it is possible to obtain the magnetic field distribution of the surface of the monitoring object pipeline 110.

The array of the effective values expressed is transmitted to the measurement managing apparatus 210, and the calculating unit 211 of the measurement managing apparatus 210 calculates the thinning distribution by the virtual eddy current method (STEP S205). Subsequently, on the basis of change in the thinning distribution or the like, the next measurement timing is set (STEP S206).

Also, the calculating unit 211 visualizes the shape and depth of thinning, on the basis of the position of the thinning (STEP S207). The visualization is performed by color mapping, three-dimensional mapping, or the like with the monitoring object pipeline 110. The shape, size, and position of the thinning, and the mapping result are recorded in the storage unit 213, and are output on a display screen or the like if necessary (STEP S208).

Figure 11:
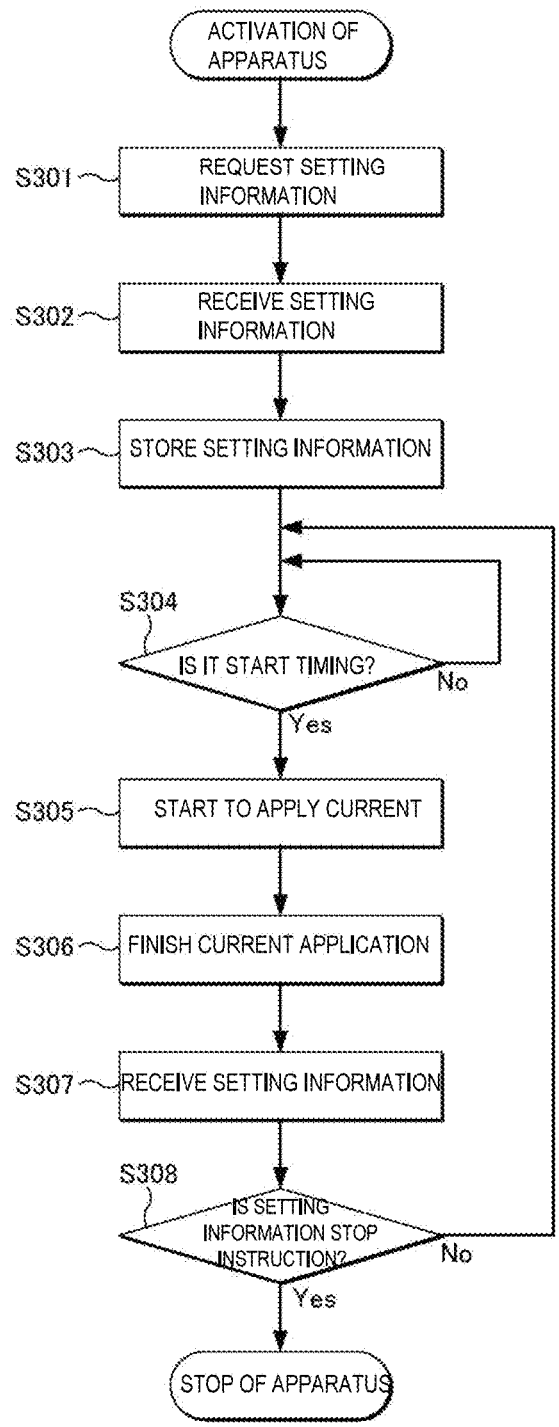
FIG. 11 is a flow chart for explaining an operation of the current applying apparatus.

Now, specific operations of the individual apparatuses will be described. First, the operation of the current applying apparatus 120 will be described with reference to a flow chart of FIG. 11. If the current applying apparatus 120 is activated, it requests setting information from the measurement managing apparatus 210 through the wireless sensor network 280 by the wireless communication unit 126 (STEP S301).

The current applying apparatus receives the setting information, as a response to the request, from the measurement managing apparatus 210 (STEP S302), and records the setting information in the storage unit 124 (STEP S303). The setting information includes the frequency, current value, application start timing (period), current application duration, and the like of an AC current to be applied.

If the current application start timing represented by the setting information comes ("Yes" in STEP S304), the current applying apparatus starts to apply the current (STEP S305). At this time, the current applying apparatus may notify the measurement managing apparatus 210 that application of the current has started.

If the current application duration represented by the setting information elapses, the current applying apparatus finishes the current application (STEP S306). At this time, the current applying apparatus may notify the measurement managing apparatus 210 that the current application has finished.

The current applying apparatus 120 further receives setting information related to the next measurement timing from the measurement managing apparatus 210 (STEP S307), and waits for the next start time (STEP S304). However, if the setting information is a stop instruction ("Yes" in STEP S308), the current applying apparatus stops.

Figure 12:
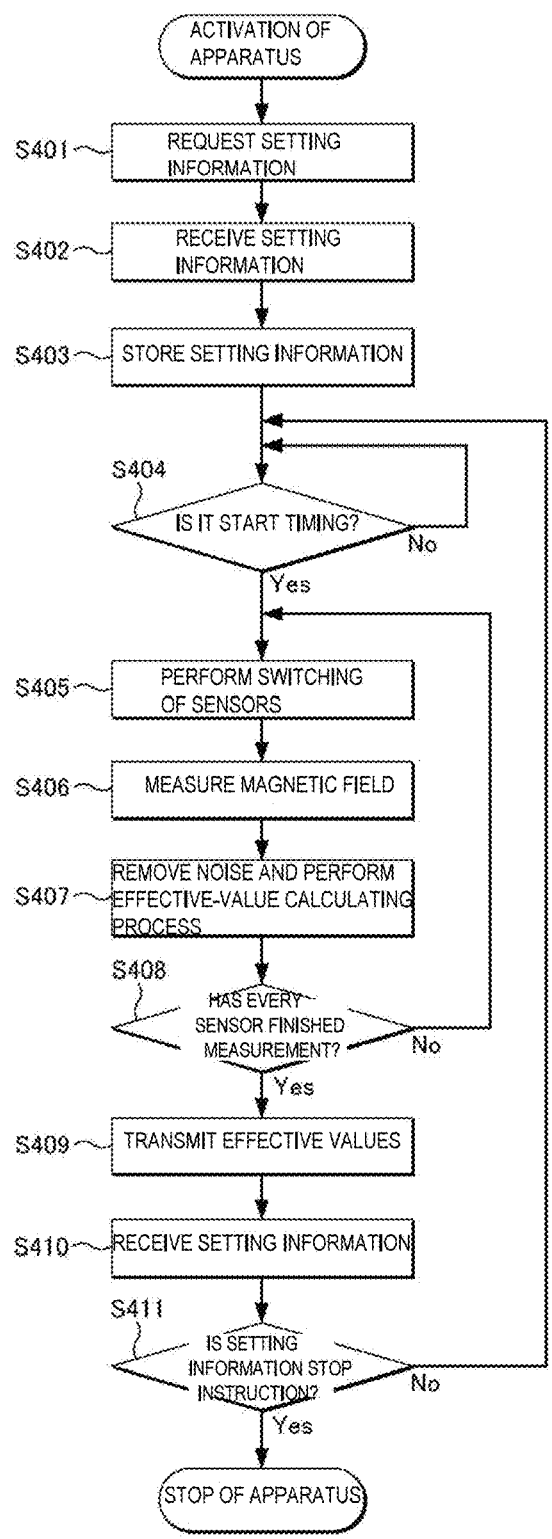
FIG. 12 is a flow chart for explaining an operation of the magnetic-field measuring apparatus.

Now, the operation of the magnetic-field measuring apparatus 130 will be described with reference to a flow chart of FIG. 12. If the magnetic-field measuring apparatus 130 is activated, it requests setting information from the measurement managing apparatus 210 through the wireless sensor network 280 by the wireless communication unit 137 (STEP S401).

The magnetic-field measuring apparatus receives the setting information, as a response to the request, from the measurement managing apparatus 210 (STEP S402), and records the setting information in the storage unit 135 (STEP S403). The setting information includes a measurement start timing (period), a measurement time per one sensor, and the frequency and the like of an AC current to be applied by the current applying apparatus 120.

If the measurement start timing represented by the setting information ("Yes" in STEP S404), the magnetic-field measuring apparatus performs switching to magnetic sensors 131 for performing measurement (STEP S405), and measures a magnetic field (STEP S406). At this time, the magnetic-field measuring apparatus may notify the measurement managing apparatus 210 that magnetic-field measurement has started.

If the measurement time per one magnetic sensor represented by the setting information elapses, the magnetic-field measuring apparatus finishes the measurement of the corresponding magnetic sensors 131, and performs the process of removing noise and calculating effective values (STEP S407). If there is any magnetic sensor 131 which has not performed measurement ("No" in STEP S408), the magnetic-field measuring apparatus performs switching of the magnetic sensors 131 (STEP S405), and repeats the measuring process.

If every magnetic sensor 131 finishes measurement ("Yes" in STEP S408), the magnetic-field measuring apparatus arranges the effective values in an array form corresponding to the magnetic sensor array 131A, and transmits the effective value array to the measurement managing apparatus 210 (STEP S409).

The magnetic-field measuring apparatus 130 further receives setting information related to the next measurement timing from the measurement managing apparatus 210 (STEP S410), and waits for the next start timing (STEP S404). However, if the setting information is a stop instruction ("Yes" in STEP S411), the magnetic-field measuring apparatus stops.

Now, the noise removing process which the calculating unit 132 of the magnetic-field measuring apparatus 130 performs in STEP S407 will be described. Since AC magnetic-field signals which the magnetic-field measuring apparatus 130 measures generally include noise, it is required to remove the noise and then perform conversion into effective values. As noise removing methods, the following four method can be considered.

First Noise Removing Method

The present method is a method of converting a measured AC signal into a frequency domain by discrete Fourier transform or Z-transform, and extracts a frequency applied by the current applying apparatus 120 from the frequency domain.

Second Noise Removing Method

The present method is a method of extracting only a regression parameter kQ by converting a measured AC signal into a frequency domain by discrete Fourier transform or Z-transform, and performing smoothing in order to cancel high-order noise, and performing regression according to Expression 5. Since the present method uses instantaneous values of a signal string which is a desired noise removal object, it is unnecessary to hold the signal on a memory, and it becomes possible to reduce the usage of a RAM of the storage unit 135.

$$\sum_{i=0}^{2} \frac{k_i}{t^i} \qquad \text{[Expression 5]}$$

More specifically, the second noise removing method is a method obtained by improving the first noise removing method using discrete Fourier transform according to the object of the present invention. Improvement points are the following two points.

Frequency resolution is good.

Only a designated frequency component is extracted, and information related to the other frequencies are not obtained.

In the first noise removing method, in order to improve the resolution of frequencies to be extracted, a measurement time should be set so as to be long. However, in the thinning detection system 10, in terms of the power consumption of the current applying apparatus 120 and the magnetic-field measuring apparatus 130, it is not preferable to set a measurement time so as to be long. In contrast, it is only needed to calculate only specific frequency components, and it is unnecessary to calculate the other frequency components. The second noise removing method is a method obtained by improving the first noise removing method such that both of frequency resolution and a measurement time are satisfactory.

The principle of the second noise removing method will be described. A signal f(t) having frequency components only in the vicinity of an angular frequency $\omega_0$ can be expressed as Expression 6. In Expression 6, $\omega_i \approx \omega_0$ is assumed.

$$f(t) = \sum_{i=0}^{N} w_i \cos(\omega_i t + \phi_i) \qquad \text{[Expression 6]}$$

In this case, it is required to obtain an amplitude $w_0$ corresponding to the angular frequency $\omega_0$. Fourier Integral of the signal f(t) in the interval of $0 \le t \le T$ can be calculated by Expression 7.

$$F[f](\omega_0) = \frac{1}{T}\int_0^T f(t)e^{i\omega_0 t}dt \qquad \text{[Expression 7]}$$

F[f]($\omega_0$) converges to $\omega_0$ as T→∞. The first noise removing method is a method of calculating this integral value. The above-described expression can be developed into Expression 8.

$$F[f](\omega_0) = w_0 + \frac{\alpha}{\omega_0 T} + \frac{\beta}{\omega_0^2 T^2} + \text{[Vibrational Term]} \qquad \text{[Expression 8]}$$

Therefore, it is possible to converge F[f]($\omega_0$) to $\omega_0$ without increasing T to ∞, by the following two processes.

A process of canceling the vibrational term by performing averaging

A process of extracting only a parameter $k_0$ by performing regression using the regression expression, that is, Expression 5

Figure 13:
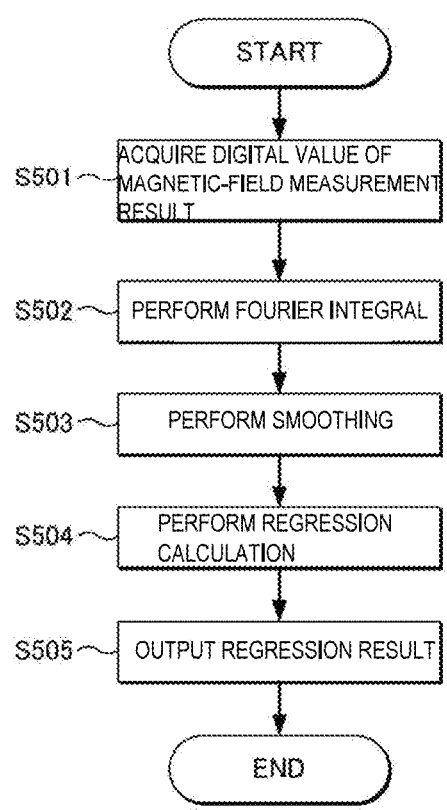
FIG. 13 is a flow chart for explaining an example of noise removal.

These processes are shown as a flow chart in FIG. 13. In other words, the digital value of the magnetic-field measurement result is acquired (STEP S501), and Fourier integral is performed (STEP S502). Subsequently, smoothing is performed (STEP S503), and a regression calculation is performed (STEP S504), and a regression result is output (STEP S505). Also, a case where the assumed condition "$\omega_i \approx \omega_0$" is not satisfied means that a component corresponding to the angular frequency $\omega_0$ is equal to 0, and thus $\omega_0$=0 is obtained without performing smoothing and regression.

Third Noise Removing Method

The present method is a method of applying a Kalman filter on the assumption that noise is normally distributed since a main component of the noise is noise which is generated by circuits of the magnetic-field measuring apparatus 130.

Fourth Noise Removing Method

The present method is a method of applying a particle filter on the assumption that an object system is linear since a main component of noise is noise which is generated by circuits of the magnetic-field measuring apparatus 130.

The magnetic-field measuring apparatus 130 performs one of the above-described noise removing methods on AC signals measured by the magnetic sensors of the magnetic sensor array 131A, and calculates effective values of the AC signals, and transmits the effective values to the measurement managing apparatus 210 through the wireless sensor network 280. However, other noise removing methods may be used.

Figure 14:
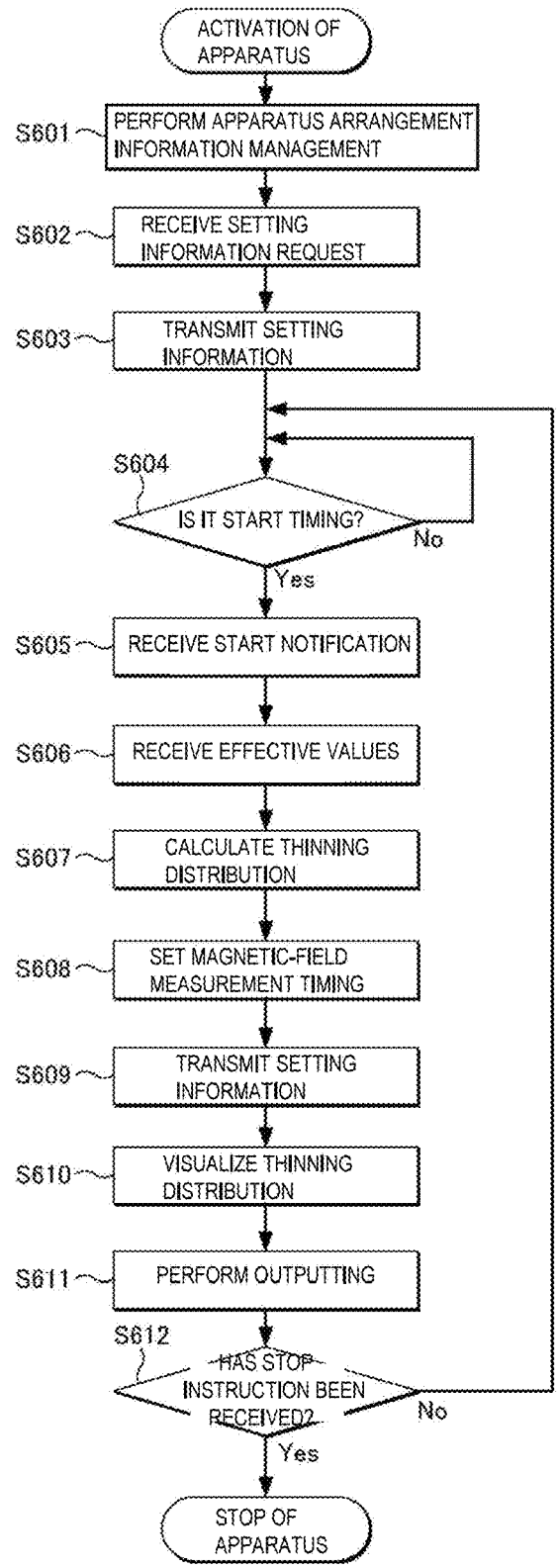
FIG. 14 is a flow chart for explaining an operation of the measurement managing apparatus.

Now, the operation of the measurement managing apparatus 210 will be described with reference to a flow chart of FIG. 14. The measurement managing apparatus 210 refers to a variety of information on apparatus arrangement recorded in the storage unit 213, such as the relative position relation between the electrodes 111 installed on the monitoring object pipeline 110 and the magnetic sensors of the magnetic sensor array 131A, and the shape of the monitoring object pipeline 110, as apparatus arrangement information (STEP S601).

If a setting information request is received from another apparatus (STEP S602), the measurement managing apparatus transmits the setting information recorded in advance in the storage unit 213 (STEP S603). Specifically, in a case of receiving a setting information request from the current applying apparatus 120, the measurement managing apparatus transmits the frequency, current value, application start timing (period), current application duration, and the like of an AC current to be applied, as setting information, and in a case of receiving a setting information request from the magnetic-field measuring apparatus 130, the measurement managing apparatus transmits the measurement start timing (period), the measurement time per one magnetic sensor, the frequency of the AC current to be applied by the current applying apparatus 120, as setting information.

If the measurement start timing represented by the setting information comes ("Yes" in STEP S604), the measurement managing apparatus receives start notifications from the current applying apparatus 120 and the magnetic sensor 131 (STEP S605). Also, the measurement managing apparatus receives the array of the effective values as the measurement result from the magnetic-field measuring apparatus 130 (STEP S606).

Subsequently, the calculating unit 211 of the measurement managing apparatus 210 calculates the thinning distribution on the basis of the measurement magnetic-field distribution received from the magnetic-field measuring apparatus 130 (STEP S607).

Figure 15:
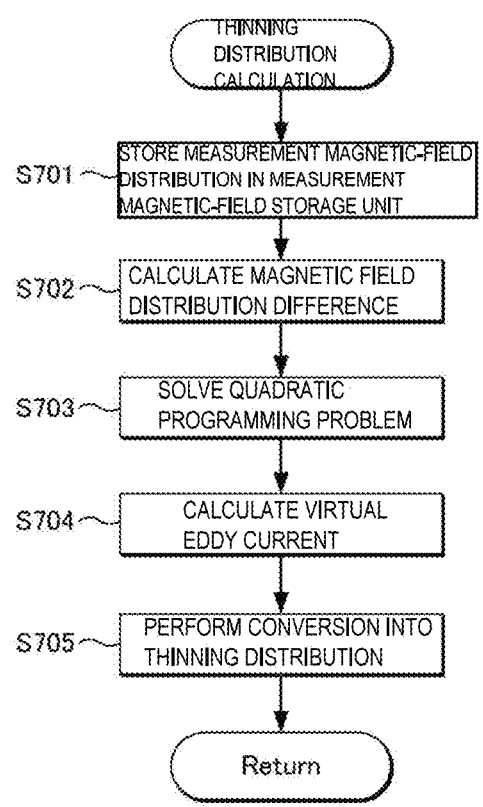
FIG. 15 is a flow chart for explaining a thinning distribution calculation process.

FIG. 15 is a flow chart for explaining a specific procedure of the thinning distribution calculation process which is performed by the calculating unit 211. First, the received measurement magnetic-field distribution is stored in the measurement magnetic-field storage unit 312 (STEP S701).

Subsequently, the difference calculating unit 321 calculates the magnetic-field distribution difference b which is the difference between the reference magnetic-field distribution stored in the reference magnetic-field storage unit 313 and the measurement magnetic-field distribution (STEP S702). The quadratic programming problem solving unit 322 solves the quadratic programming problem P (STEP S703), and calculates the virtual current distribution x (STEP S704), and the thinning-distribution calculating unit 323 converts the virtual current distribution x into a thinning distribution D (STEP S705).

Returning to FIG. 14, if the thinning distribution is calculated from the measurement magnetic-field distribution which is the array of the effective values (STEP S607), the calculating unit 211 of the measurement managing apparatus 210 sets the next measurement timing on the basis of change in the shape and size of the thinning and the like (STEP S608).

Specifically, from the shape and size of the thinning the calculating unit calculates the depth in the thickness direction and the sectional loss rate. Also, the calculating unit calculates the change rates per unit time by comparing them with the thinning depth and the sectional loss rate measured at the previous time. Further, the calculating unit calculates the temporal margins by comparing them with the minimum allowable thickness and the maximum allowable shearing stress, and sets the next measurement timing for the current applying apparatus 120 and the magnetic-field measuring apparatus 130, on the basis of a smaller one of those margins.

Figure 16:
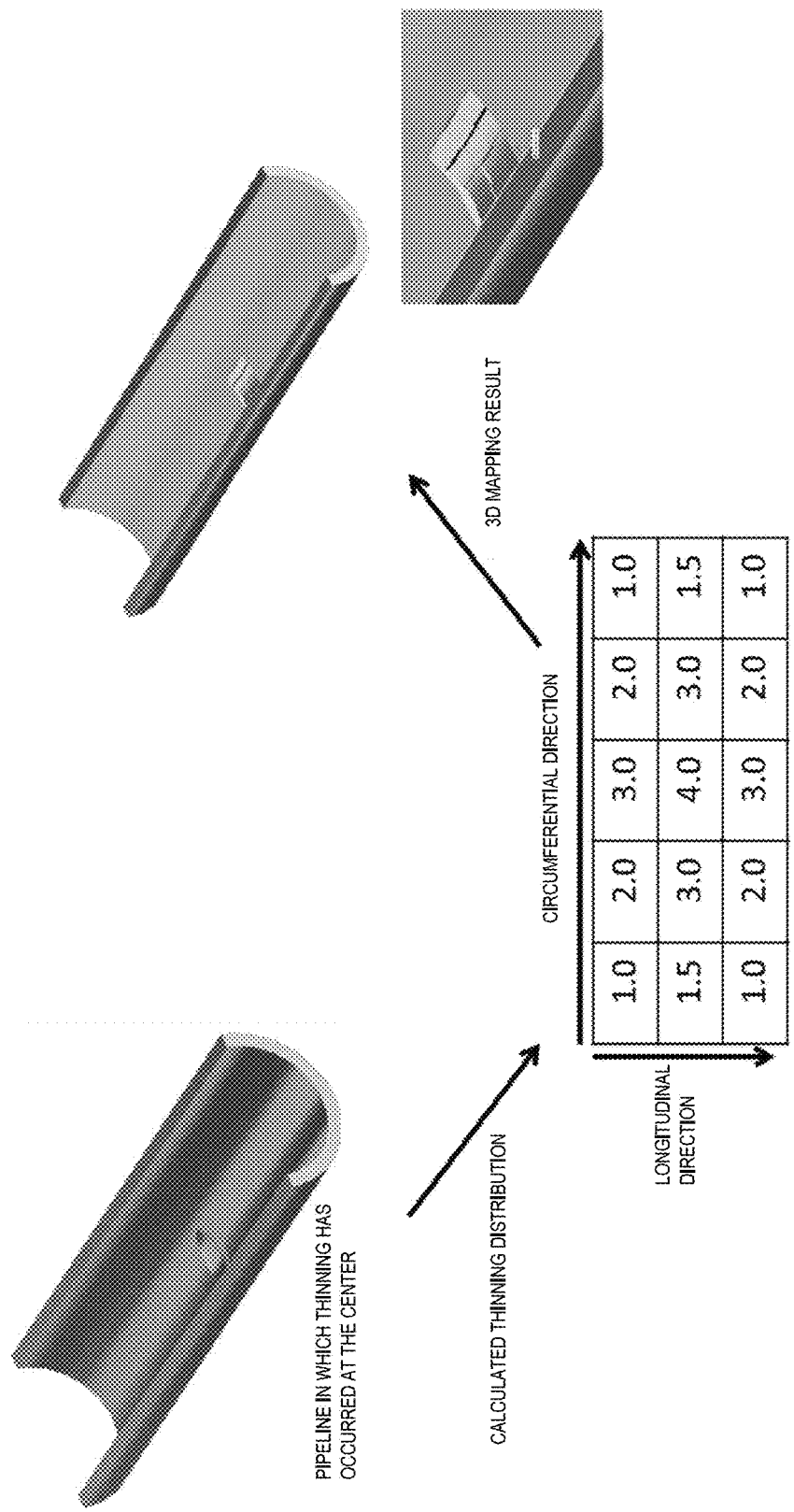
FIG. 16 is a view illustrating an example of three-dimensional mapping.

Furthermore, the calculating unit 211 visualizes the calculated thinning distribution (STEP S610). The visualization of the thinning distribution is performed, for example, by three-dimensional mapping with the monitoring object pipeline 110. FIG. 16 shows an example of three-dimensional mapping performed on the basis of the calculated thinning distribution.

The measurement managing apparatus records the thinning distribution and the result of the three-dimensional mapping in the storage unit 213, and outputs them on a display screen or the like if necessary (STEP S611). If any stop instruction has not been received ("No" in STEP S612), the measurement managing apparatus waits for the next start time (STEP S604); whereas if a stop instruction has been received ("Yes" in STEP S612), the measurement managing apparatus stops. At this time, the measurement managing apparatus transmits stop setting information to the current applying apparatus 120 and the magnetic-field measuring apparatus 130.

Meanwhile, in the thinning detection system 10 of the present embodiment, it is required to manage the positions of the monitoring object pipeline 110, the magnetic sensor array 131A of the magnetic-field measuring apparatus 130, and the electrodes 111 of the current applying apparatus 120 during installation, attachment, or detachment, and manage their relative positions, on the basis of the characteristics of the method of converting the calculated magnetic field distribution into the thinning distribution. The reason is that the density of a magnetic field changes according to a distance from the generation source to a measurement point, and this emerges as an error during conversion.

For this reason, as described above, it is preferable that the mounting member of the magnetic sensor 131 come into point contact with the monitoring object pipeline 110 and have toughness.

However, according to temporal change of equipment, the relative position between the magnetic sensor array 131A and the monitoring object pipeline 110 may be shifted, and places where they are actually mounted may be deviated from their positions in the system design. In a case where such a deviation occurs, it is possible to prevent occurrence of an error by correcting the measurement values of the magnetic sensors 131 according to the deviation amount.

For example, in a case of a deviation in the x axis direction or the y axis direction (on a plane parallel to the surface of the monitoring object pipeline 110), as the correction method, a method of correcting the measurement values of the magnetic sensors 131 by an existing technology such as linear supplementation or bicubic supplementation using the measurement values of neighboring magnetic sensors 131 on the basis of the deviation amount of the actual positions of the magnetic sensors 131 from the original positions of the magnetic sensors 131 can be considered.

Also, in a case of a deviation in the z axis direction (in a direction perpendicular to the surface of the monitoring object pipeline 110), since measurement values are inversely proportional to the square of distance, for example, if the deviation amount of the actual positions of the magnetic sensors 131 is 1.5 times that of the original positions of the magnetic sensors 131, it is possible to perform correction by multiplying the measurement values by the square of 1.5.

As a method of acquiring the actual positions of the magnetic sensors 131, a method of using a 3D scanner can be considered; however, the positions of the magnetic sensors in the z axis direction can also be acquired on the basis of the measurement values of the magnetic sensors 131.

This is a method of using skin effect in which an AC current flowing in a conductor is concentrated to the surface of the conductor as frequency increases, resulting in a decrease in the current density of the inside. In general, a distance at which the current density of a conductor becomes 1/e times that of the surface is called its skin depth, and if a frequency is determined, it is possible to specify the skin depth of that conductor.

Figure 17A:
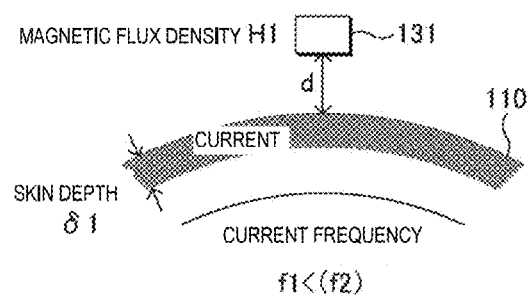
FIGS. 17A and 17B are views for explaining a method of measuring a distance between a monitoring object pipeline and a magnetic sensor.
Figure 17B:
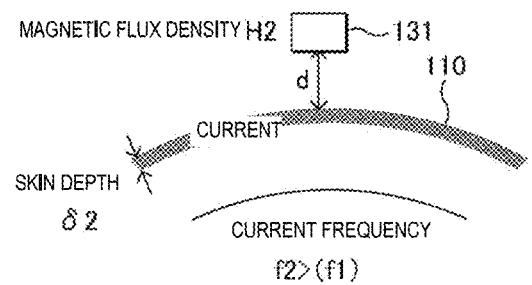

Specifically, as shown in FIG. 17A, it is assumed that a magnetic flux density H1 is measured by a magnetic sensor 131 when an AC current having a frequency f1 flows in the monitoring object pipeline 110. In this case, a skin depth $\delta_1$ is known. Also, as shown in FIG. 17B, it is assumed that a magnetic flux density H2 is measured by the magnetic sensor 131 when an AC current having a frequency f2 higher than the frequency f1 flows in the monitoring object pipeline 110. In this case, a skin depth $\delta_2$ is known, and is shallower than the skin depth δ1. Also, the frequency f1 is selected such that, even if a part is thinned, the skin depth δ1 does not reach the thinned part.

In this case, if a distance between the monitoring object pipeline 110 and the magnetic sensor 131 is represented by d, Expression 9 is established. In Expression 9, k is a constant which is determined by the applied current, the monitoring object pipeline 110, and the like.

$$H1 = \frac{k}{\left(d + \frac{\delta 1}{2}\right)^2},$$ [Expression 9]

$$H2 = \frac{k}{\left(d + \frac{\delta 2}{2}\right)^2}$$

If Expression 9 is solved in terms of d, k is eliminated, whereby it is possible to obtain Expression 10. Therefore, it is possible to acquire the position of the magnetic sensor 131 relative to the monitoring object pipeline 110.

$$d = \frac{\delta 1 - \delta 2 \sqrt{H1/H2}}{2\left(\sqrt{H1/H2} - 1\right)}$$ [Expression 10]

Figure 18:
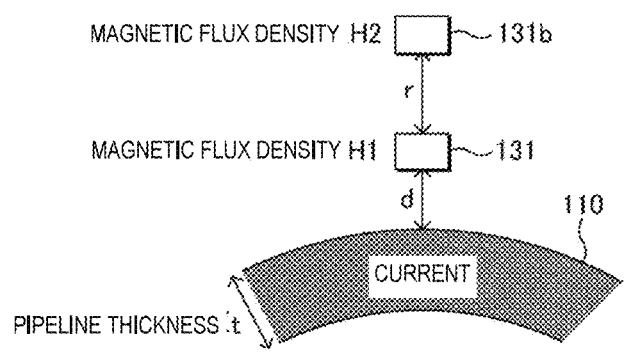
FIG. 18 is a view for explaining the method of measuring a distance between a monitoring object pipeline and the magnetic sensor.

Alternatively, even if an auxiliary magnetic sensor 131b is disposed above the magnetic sensor 131 as shown in FIG. 18, it is possible to acquire the position of the magnetic sensor 131 relative to the monitoring object pipeline 110. Here, a distance between the magnetic sensor 131 and the auxiliary magnetic sensor 131b is represented by r, and it is assumed that this distance r is firmly maintained by the mounting member and the like and does not change. Also, the thickness of the monitoring object pipeline 110 is represented by t.

In a case where an AC current flows in the monitoring object pipeline 110 (wherein skin effect may or may not be considered), and a magnetic flux density H1 is measured by the magnetic sensor 131, and a magnetic flux density H2 is measured by the auxiliary magnetic sensor 131b, Expression 11 is established. In Expression 11, k is a constant which is determined by the applied current, the monitoring object pipeline 110, and the like.

$$H1 = \frac{k}{\left(d + \frac{t}{2}\right)^2},$$ [Expression 11]

$$H2 = \frac{k}{\left(d + \frac{t}{2} + r\right)^2}$$

If Expression 11 is solved in terms of d, k is eliminated, whereby it is possible to obtain Expression 12. Therefore, it is possible to acquire the position of the magnetic sensor 131 relative to the monitoring object pipeline 110.

$$d = \frac{r}{2\left(\sqrt{H1/H2} - 1\right)} - \frac{t}{2}$$ [Expression 12]

If the distance d obtained in the above-described manner is different from the original distance, it is possible to perform correction according to the difference on the measurement value, thereby capable of preventing a decrease in the accuracy of thinning distribution estimation.

In this case, in order to derive the relative positions of the sensors to the pipeline and correction coefficients, calculations are approximately performed using the concept of the center of electric current. Therefore, all of the correction coefficients of Expressions 9 and 11 are inversely proportional to the square of distance. However, without using the concept of the center of electric current, for example, a precise calculation of a current distribution, a numerical value simulation, or the like can also be used to derive a more practical correction formula.

What is claimed is:

1. A thinning detection system comprising:
   a current applying apparatus configured to apply an AC current to electrodes installed on metal equipment which is a monitoring object;
   a magnetic-field measuring apparatus including an array of magnetic sensors configured to measure a magnetic field distribution of a surface side of the metal equipment; and
   a measurement managing apparatus configured to estimate a thinning distribution of the metal equipment on the basis of a magnetic field distribution difference which is a difference between a reference magnetic-field distribution which is obtained in a case where thinning has not occurred in the metal equipment and a measurement magnetic-field distribution which is an actual measurement result,
   wherein the measurement managing apparatus calculates a virtual current distribution of the metal equipment from the magnetic field distribution difference, and estimates the thinning distribution of the metal equipment on the basis of a virtual eddy current represented by the virtual current distribution,
   wherein the virtual eddy current is a difference between a first current distribution which is obtained in a case in which thinning has not occurred in the metal equipment and a second current distribution which is obtained in a case in which thinning has occurred in the metal equipment, and
   wherein the measurement managing apparatus is configured to:
      estimate a thinning shape on the basis of a spiral shape of the virtual eddy current; and
      estimate a thinning depth on the basis of a density of the virtual eddy current.

2. The thinning detection system according to claim 1, wherein:
   the measurement managing apparatus is configured to:
      approximate a current path of the metal equipment by an oriented square lattice; and
      calculate the virtual current distribution by solving a quadratic programming problem for minimizing a distance between the magnetic field distribution difference and a magnetic flux density distribution on each magnetic sensor caused by the virtual current distribution under a constraint condition which is a current conservation law for each node of the oriented square lattice.

3. The thinning detection system according to claim 1, wherein:

the measurement managing apparatus is configured to correct the measurement magnetic-field distribution on the basis of positions of the magnetic sensors and the metal equipment.

4. The thinning detection system according to claim 3, wherein:
with respect to a certain magnetic sensor, on the basis of magnetic flux densities obtained by AC currents with different frequencies applied to the metal equipment, the measurement managing apparatus is configured to calculate the positions of the corresponding magnetic sensor and the metal equipment.

5. The thinning detection system according to claim 3, wherein:
the measurement managing apparatus is configured to calculate the positions of a certain magnetic sensor and the metal equipment on the basis of a magnetic flux density measured by the corresponding magnetic sensor, and a magnetic flux density measured by an auxiliary magnetic sensor disposed on the extension of the corresponding magnetic sensor from the metal equipment.

6. A thinning detection method comprising:
applying an AC current to electrodes installed on metal equipment which is a monitoring object;
measuring a magnetic field distribution of a surface side of the metal equipment by an array of magnetic sensors; and
estimating a thinning distribution of the metal equipment on the basis of a magnetic field distribution difference which is a difference between a reference magnetic-field distribution which is obtained in a case where thinning has not occurred in the metal equipment and a measurement magnetic-field distribution which is an actual measurement result,
wherein the thinning estimation calculates a virtual current distribution of the metal equipment from the magnetic field distribution difference, and estimates the thinning distribution of the metal equipment on the basis of a virtual eddy current represented by the virtual current distribution,
wherein the virtual eddy current is a difference between a first current distribution which is obtained in a case in which thinning has not occurred in the metal equipment and a second current distribution which is obtained in a case in which thinning has occurred in the metal equipment, and
wherein the estimating comprises:
estimating a thinning shape on the basis of a spiral shape of the virtual eddy current; and
estimating a thinning depth on the basis of a density of the virtual eddy current.

7. The thinning detection system according to claim 1, wherein the thinning distribution comprises a position, shape and depth.

8. The thinning detection system according to claim 1, wherein the virtual eddy current comprises a current density and a spiral direction.

* * * * *